(12) United States Patent
Kim et al.

(10) Patent No.: US 7,632,748 B2
(45) Date of Patent: Dec. 15, 2009

(54) SEMICONDUCTOR DEVICE HAVING A FUSE BARRIER PATTERN AND FABRICATION METHOD THEREOF

(75) Inventors: Do-Wan Kim, Seoul (KR); Sung-Joon Park, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 405 days.

(21) Appl. No.: 11/401,435

(22) Filed: Apr. 10, 2006

(65) Prior Publication Data
US 2007/0023860 A1    Feb. 1, 2007

(30) Foreign Application Priority Data
Jul. 12, 2005    (KR) .................. 10-2005-0062866

(51) Int. Cl.
*H01L 21/44* (2006.01)
(52) U.S. Cl. ...................... 438/601; 257/529
(58) Field of Classification Search ........... 438/132, 438/215, 281, 333, 467, 601; 257/529
See application file for complete search history.

(56) References Cited

U.S. PATENT DOCUMENTS 4,536,949 A * 8/1985 Takayama et al. ........... 438/601
5,729,041 A * 3/1998 Yoo et al. .................. 257/529
2005/0236688 A1* 10/2005 Bang et al. ................. 257/529

FOREIGN PATENT DOCUMENTS

| JP | 08-172134 | 7/1996 |
|---|---|---|
| KR | 10-2002-0024460 | 3/2002 |
| KR | 10-2004-0008484 | 1/2004 |

* cited by examiner

*Primary Examiner*—W. David Coleman
*Assistant Examiner*—Sonya D McCall-Shepard
(74) *Attorney, Agent, or Firm*—Mills & Onello, LLP

(57) ABSTRACT

In a semiconductor device having a plurality of fuses and a method of fabricating the same, the semiconductor device comprises an inter-layer dielectric layer on a semiconductor substrate; a plurality of fuses on the inter-layer dielectric layer, an inter-metallic dielectric layer on the plurality of fuses and the inter-layer dielectric layer, a passivation layer on the inter-metallic dielectric layer, fuse windows exposing portions of a top surface and sidewall surfaces of the plurality of fuses, and a fuse barrier pattern between adjacent ones of the plurality of the fuses.

19 Claims, 8 Drawing Sheets

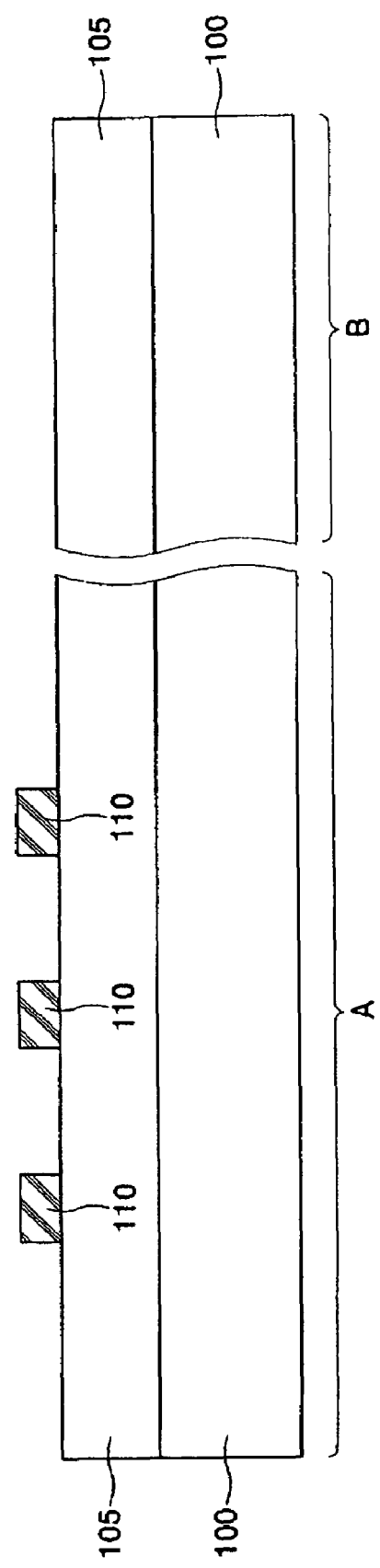

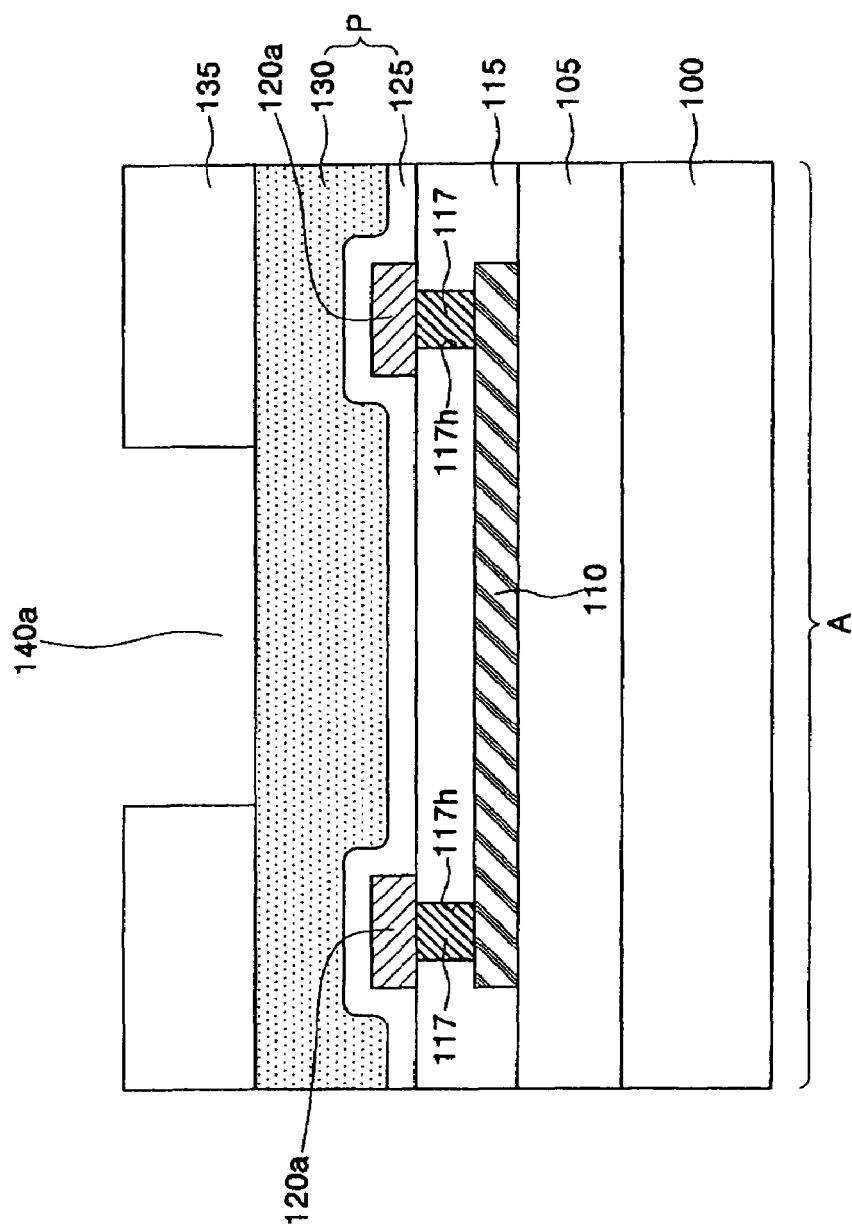

SEMICONDUCTOR DEVICE HAVING A FUSE BARRIER PATTERN AND FABRICATION METHOD THEREOF

RELATED APPLICATION

This application claims priority to Korean Patent Application number 10-2005-0062866, filed in the Korean Intellectual Property Office on Jul. 12, 2005, the contents of which are incorporated herein in their entirety by reference.

BACKGROUND OF THE INVENTION

1. Field of the Invention

The present invention relates to a semiconductor device having a fuse barrier pattern and a fabrication method thereof. More particularly, the present invention relates to a semiconductor device having a fuse barrier pattern that is located between each fuse in a fuse region of the semiconductor device and a fabrication method thereof.

2. Description of the Related Art

Semiconductor memory devices are commonly tested using an electrical tester in a wafer-level state before they are assembled into a package-level state. As the result of the testing, they can be sorted into properly functioning chips and malfunctioning chips.

If the malfunctioning chips have just a few failing cells, the cells that are identified as failing can be repaired by exchanging the failing cells with redundant cells. Such a repair process commonly includes a fuse blowing step that employs a laser beam in order to reassign the failing cells with the new addresses of the redundant cells for data reading and writing.

In the case of conventional semiconductor memory devices, the fuses are generally formed in the same fabrication step with the formation of bit-lines or word-lines. Therefore, the fuses are commonly formed at the same elevation as those of the bit-lines or word-lines. A dielectric layer is deposited on the resulting fuse.

FIG. 1 is a cross-sectional view illustrating a fuse region of a conventional semiconductor memory device.

Referring to FIG. 1, a dielectric layer 12 is deposited on a semiconductor substrate 10. A plurality of fuses 15 are formed on the dielectric layer. An inter-metallic dielectric layer 20 is formed on the plurality of fuses 15. In order to blow, open, or cut, the plurality of fuses, a fuse window 25 is formed in the inter-metallic dielectric layer by partially etching the inter-metallic dielectric layer 20. Therefore, a portion of the inter-metallic dielectric layer 20 remains on the plurality of fuses 15.

Repair processes can be performed by blowing one or more of the fuses with a laser beam. However, if the inter-metallic dielectric layer 20 remaining on the bottom portion of the fuse window 25 on the plurality of fuses 15 is too thick, it can be difficult to completely blow, or open, the fuse to be opened. Thus, residue of the fuse can remain in the inter-metallic dielectric layer 20, especially at the bottom sidewalls of the fuse, as shown in region S of FIG. 1.

If the energy of the laser beam is increased to a higher level in order to ensure complete opening of the fuse, an adjacent fuse that is located beside the blown fuse can be damaged by the high energy laser beam. With the continuous increase of semiconductor device integration density, the distance between each fuse continues to become smaller. As a result, it becomes more difficult to blow a fuse precisely and completely.

In order to solve this problem mentioned above in contemporary systems, the thickness of the inter-metallic dielectric layer 20 remaining on the plurality of fuses at the bottom of the fuse window 25 is made to be thinner, even if the inter-metallic dielectric layer 20 is etched in the fuse window region 25 to a degree such that the top surfaces of the plurality of fuses are exposed. In this case, even though it is possible to blow the fuse completely, the broken pieces of the blown fuse can adhere to the adjacent, non-selected, fuses which are not to be opened, thereby electrically connecting, or shorting, adjacent fuses. This, in turn, can cause the semiconductor memory device to malfunction.

SUMMARY OF THE INVENTION

The present invention is directed to a device and fabrication method of such a device wherein fuses can be blown safely and completely, and with a suitable energy range of the laser beam which is properly applied to the repair process.

The present invention further provides a method of fabricating a semiconductor memory device having a plurality of fuses including fuse barrier patterns between each fuse in order to prevent adjacent fuses from being damaged when a fuse relating to a failed cell is opened by a laser beam.

The present invention further provides a semiconductor memory device having a plurality of fuses including fuse barrier patterns between each fuse in order to prevent adjacent fuses from being damaged when a fuse relating to a failed cell is opened by a laser beam.

In one aspect, the present invention is directed to a method of fabricating a semiconductor device having a plurality of fuses, comprising: forming an inter-layer dielectric layer on a semiconductor substrate; forming a plurality of fuses on the inter-layer dielectric layer; forming an inter-metallic dielectric layer on the plurality of fuses and on the inter-layer dielectric layer; forming a passivation layer on the inter-metallic dielectric layer; forming fuse windows to expose portions of a top surface and sidewall surfaces of the plurality of fuses by etching the passivation layer and the inter-metallic dielectric layer; and forming a fuse barrier pattern between adjacent ones of the plurality of fuses.

In one embodiment, the fuse windows and the fuse barrier pattern are formed simultaneously.

In another embodiment, the fuse barrier pattern consists of a multi-layered structure of the same materials as those of the inter-metallic dielectric layer and the passivation layer.

In another embodiment, the method further comprises forming a photoresist pattern on the passivation layer before forming the fuse windows; wherein the photoresist pattern is used as a mask when the inter-metallic dielectric layer and the passivation layer are etched.

In another embodiment, the method further comprises forming a pair of via holes at end regions of each of the plurality of fuses; and filling a conductive material in the via holes to connect the fuses with conductive lines formed on the inter-metallic dielectric layer.

In another embodiment, the method further comprises forming a capping layer on the fuse barrier pattern and on the exposed portions of the plurality of fuses.

In another embodiment, the capping layer is formed of a material selected from a group consisting of a silicon oxide layer and a silicon nitride layer.

In another embodiment, the passivation layer comprises a silicon oxide layer and a silicon nitride layer.

In another embodiment, the inter-metallic dielectric layer comprises a silicon oxide layer.

In another aspect, the present invention is directed to a method of fabricating a semiconductor device having a plurality of fuses, comprising: providing a semiconductor substrate having a fuse region and a pad region; forming an inter-layer dielectric layer on the semiconductor substrate; forming a plurality of metallic fuses on the inter-layer dielectric layer in the fuse region; forming an inter-metallic dielectric layer on the plurality of fuses and on the inter-layer dielectric layer; forming a plurality of metal pads on the inter-metallic dielectric layer in the pad region; forming a passivation layer on the plurality of metal pads and on the inter-metallic dielectric layer; forming fuse windows to expose portions of a top surface and sidewall surfaces of the plurality of fuses by etching the passivation layer and inter-metallic dielectric layer; forming a fuse barrier pattern between adjacent ones of the plurality of fuses; and forming pad windows on the plurality of metal pads.

In one embodiment, the fuse windows, the fuse barrier pattern, and the pad windows are formed simultaneously by etching the passivation layer and the inter-metallic dielectric layer.

In another embodiment, the fuse barrier pattern consists of a multi-layered structure of the same material as those of the inter-metallic dielectric layer and the passivation layer.

In another embodiment, the method further comprises forming a photoresist pattern on the passivation layer before forming the fuse windows; wherein the photoresist pattern is used as a mask when the inter-metallic dielectric layer and the passivation layer are etched.

In another embodiment, the method further comprises forming a pair of via holes at end regions of each of the plurality of fuses; and filling a conductive material in the via holes to connect the fuses with conductive lines formed on the inter-metallic dielectric layer.

In another embodiment, the method further comprises forming a capping layer on the fuse barrier pattern and on the exposed portions of the plurality of fuses.

In another embodiment, the capping layer is formed of a material selected from a group consisting of a silicon oxide layer and a silicon nitride layer.

In another embodiment, the passivation layer comprises a silicon oxide layer and a silicon nitride layer.

In another embodiment, the inter-metallic dielectric layer comprises a silicon oxide layer.

In another aspect, the present invention is directed to a semiconductor device having a plurality of fuses comprising: an inter-layer dielectric layer on a semiconductor substrate; a plurality of fuses on the inter-layer dielectric layer; an inter-metallic dielectric layer on the plurality of fuses and the inter-layer dielectric layer; a passivation layer on the inter-metallic dielectric layer; fuse windows exposing portions of a top surface and sidewall surfaces of the plurality of fuses; and a fuse barrier pattern between adjacent ones of the plurality of the fuses, the fuse barrier pattern comprising a multi-layered structure of the same materials as the inter-metallic dielectric layer and the passivation layer.

In one embodiment, the device further comprises metal lines on the inter-metallic dielectric layer; and a plurality of via contact plugs connecting the metal lines with the fuses through the inter-metallic dielectric layer.

In another embodiment, the device further comprises a capping layer on the fuse barrier pattern and on the exposed portions of the plurality of fuses.

In another embodiment, the capping layer is a material selected from a group consisting of a silicon oxide layer and a silicon nitride layer.

In another embodiment, the passivation layer comprises a silicon oxide layer and a silicon nitride layer.

In another embodiment, the inter-metallic dielectric layer comprises a silicon oxide layer.

BRIEF DESCRIPTION OF THE DRAWINGS

The above features and advantages of the present invention will become more apparent to those of ordinary skill in the art by describing in detail exemplary embodiments thereof with reference to the attached drawings in which:

FIGS. 3A, 4A, and 5A are cross-sectional views taken along section line I-I' of FIG. 2 of a semiconductor device memory in accordance with an embodiment of the present invention;

FIGS. 3B, 4B, and 5B are cross-sectional views taken along section line II-II' of FIG. 2 of a semiconductor device memory in accordance with an embodiment of the present invention.

DETAILED DESCRIPTION OF THE INVENTION

Figure 1:
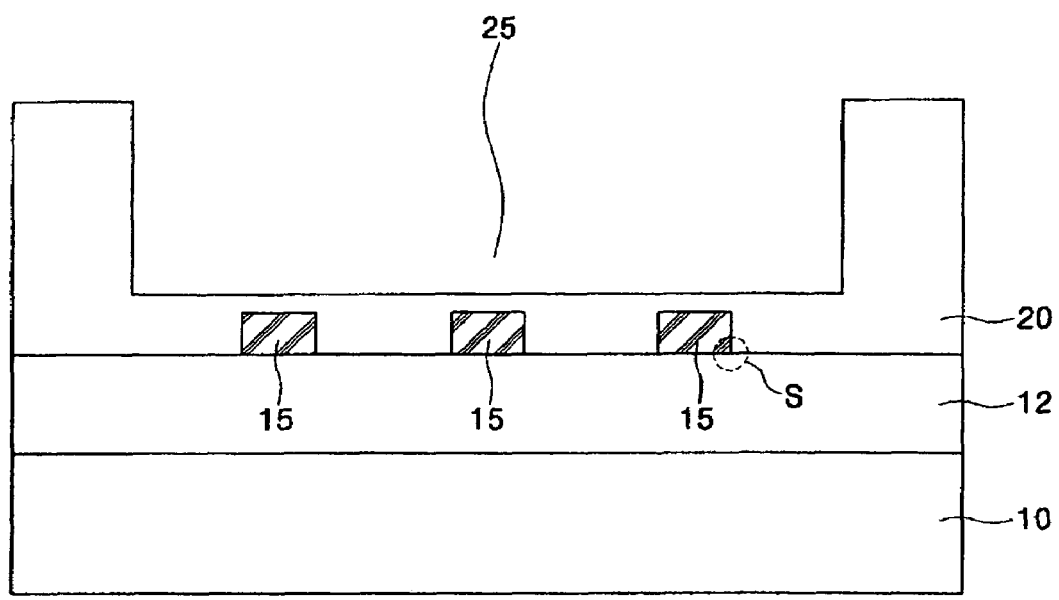
FIG. 1 is a cross-sectional view illustrating a fuse region of a conventional semiconductor memory device.

The present invention will now be described more fully hereinafter with reference to the accompanying drawings, in which exemplary embodiments of the invention are shown. The invention may, however, be embodied in different forms and should not be construed as limited to the embodiments set forth herein. Rather, these embodiments are provided so that this disclosure will be thorough and complete, and will fully convey the scope of the invention to those skilled in the art.

In the drawings, the thickness of layers and regions are exaggerated for clarity. It will also be understood that when a layer is referred to as being "on" another layer or substrate, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being "between" two layers, it can be the only layer between the two layers, or one or more intervening layers may also be present. Like reference numerals and characters in different drawings represent like elements throughout.

Figure 2:
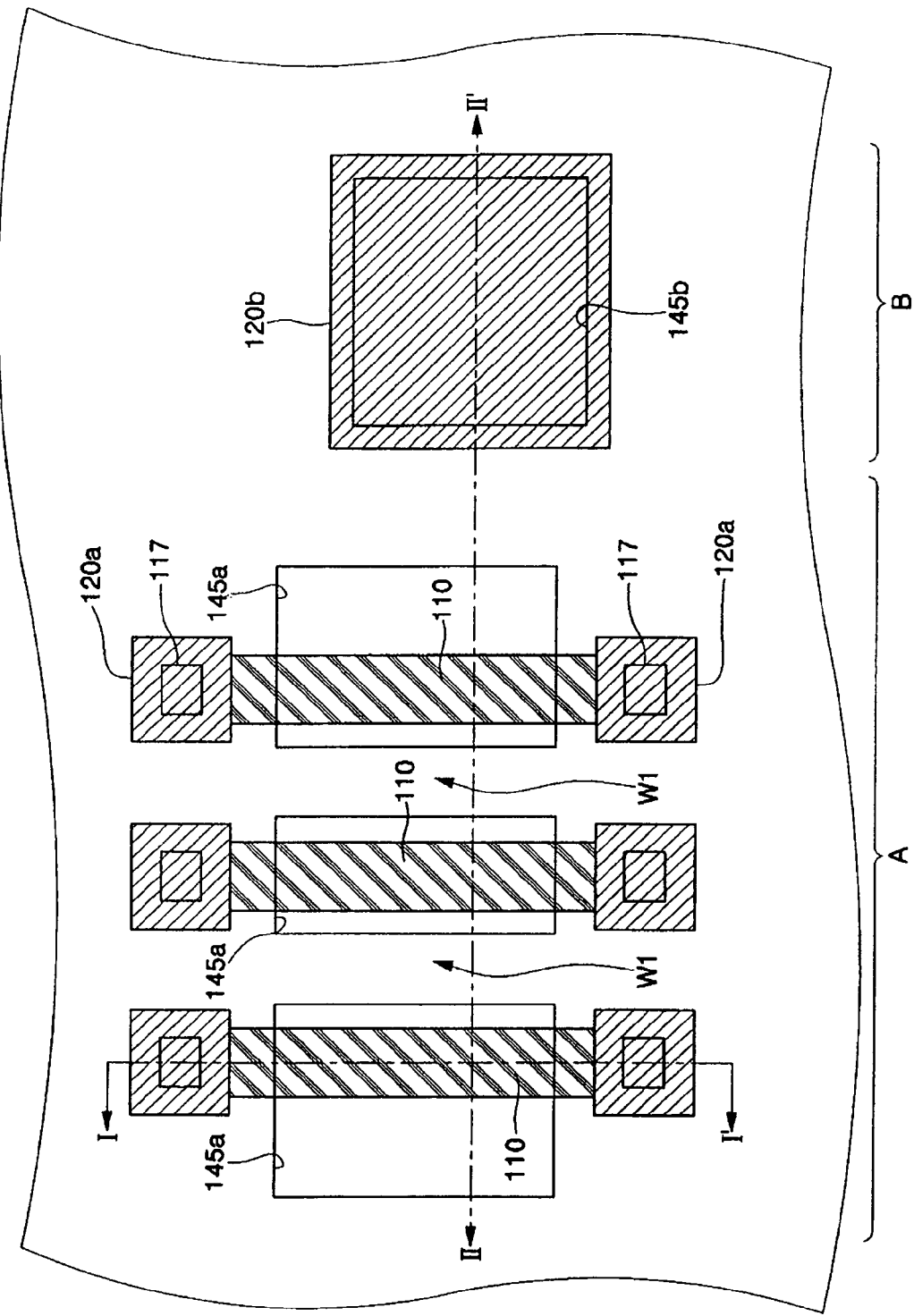
FIG. 2 is a planar layout illustrating a fuse region and a pad region in accordance with an embodiment of the present invention.
Figure 3A:
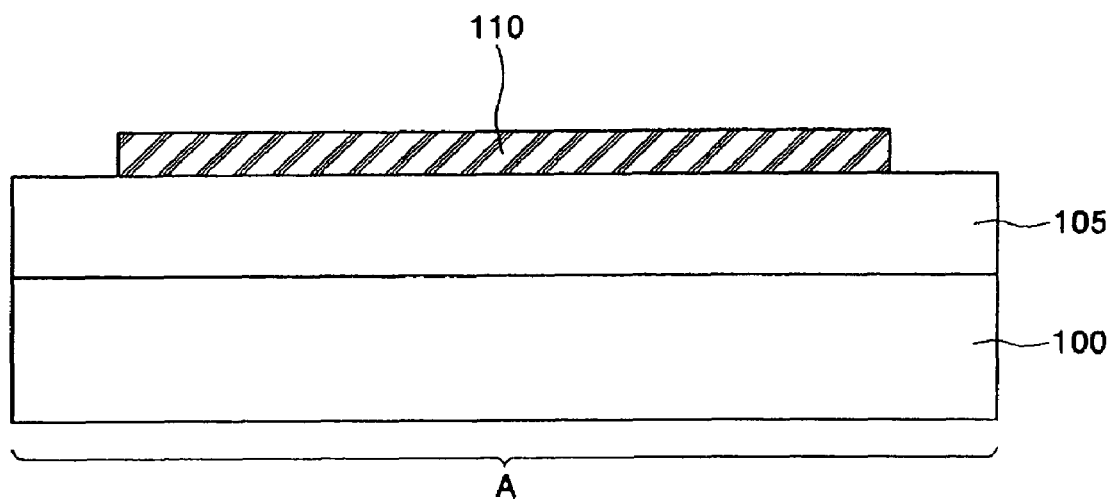

Referring to FIGS. 2, 3A, and 3B, an inter-layer dielectric layer 105 is formed on a semiconductor substrate 100. Before forming the inter-layer dielectric layer 105, various discrete devices can be formed on the semiconductor substrate, for example, transistors, capacitors, and resistors. A conductive layer is formed on the inter-layer dielectric layer 105. A plurality of fuses 110 is formed by patterning the conductive layer in the fuse region A of FIG. 2. The conductive layer can comprise at least one conductive material selected from a group consisting of a doped polysilicon layer, metal-silicide layer, metal layer, and metal-nitride layer. The plurality of fuses 110 can be formed so that their respective longitudinal axes are in parallel, as shown in FIG. 2.

Figure 4B:
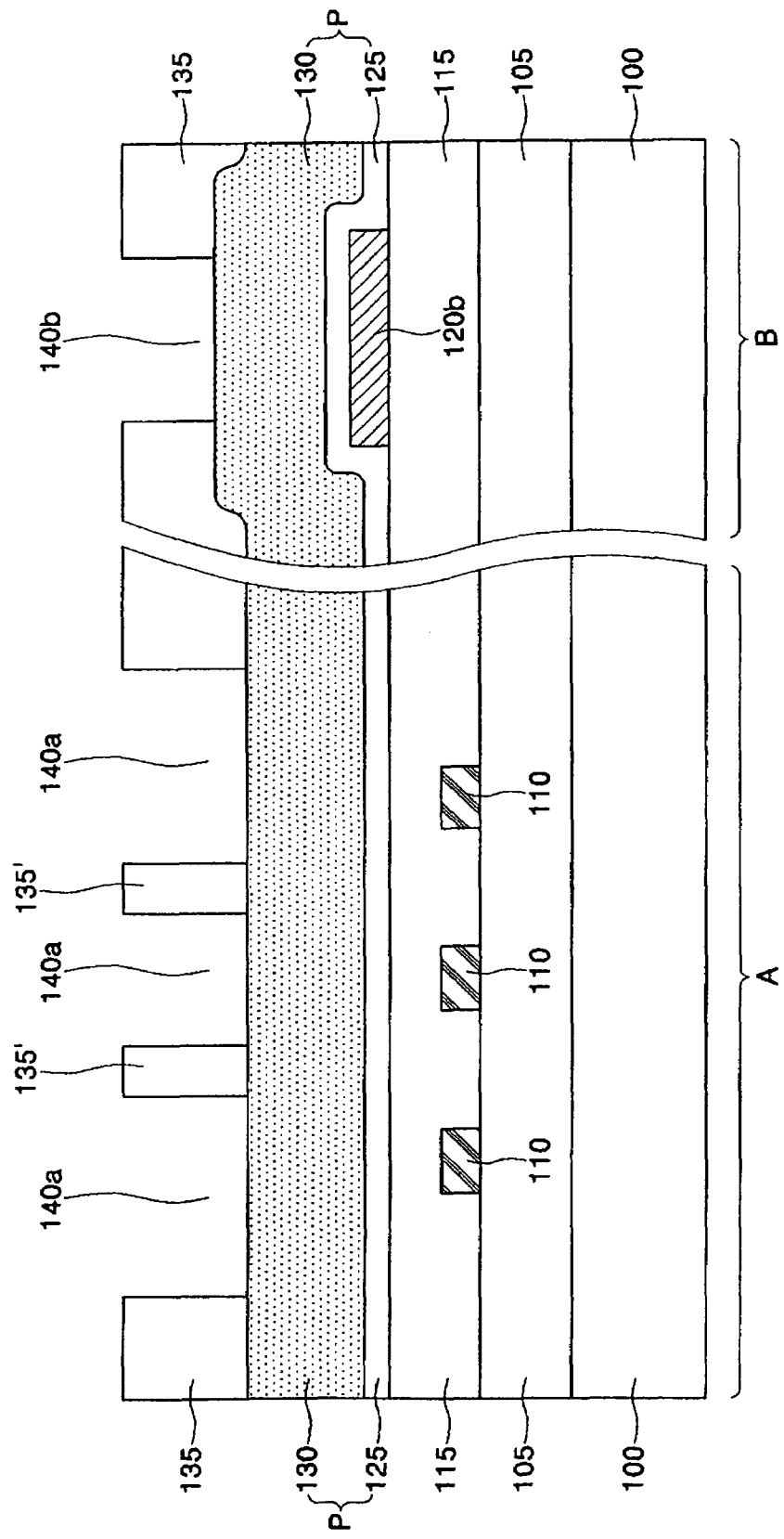

Referring to FIGS. 2, 4A, and 4B, an inter-metallic dielectric layer 115 is formed on the resulting structure, including the plurality of fuses 110. The inter-metallic dielectric layer can comprise, for example, at least one material selected from a group consisting of a HDP (High density plasma) oxide layer, TEOS (Tetra ethyl orthosilicate glass) layer, USG (Undoped silicate glass), FOX (Flow oxide) layer, and BPSG (Boro-phospho silicate glass) layer.

Contact holes 117h, that partially expose both end regions of the plurality of fuses, are formed by patterning the inter-metallic dielectric layer 115. Contact plugs 117 are formed in the contact holes 117h. Metal lines 120a, which are electrically connected with the plurality of fuses, are then formed on the contact plugs 117 and the inter-metallic dielectric layer 115. When the metal lines 120a are formed, at least one metal pad 120b is simultaneously formed on the inter-metallic dielectric layer 115 in a pad region B of the device. The metal lines 120a can comprise, for example, aluminum or aluminum alloy.

A passivation layer P is formed on the metal lines 120a and the metal pad 120b. The passivation layer P can comprise a multi-layered structure including an oxide layer 125 and a silicon nitride layer 130. The oxide layer 125 can comprise at least one material selected from a group consisting of a HDP (High density plasma) oxide layer, TEOS (Tetra ethyl orthosilicate glass) layer, USG (Undoped silicate glass), FOX (Flow oxide) layer, and BPSG (Boro-phospho silicate glass) layer.

A photoresist pattern 135 can be formed on the passivation layer P. The photoresist pattern 135 includes openings 140a which are each positioned above the plurality of fuses and pad openings 140b which are positioned above the metal pad 120b. At this time, several bar patterns 135' formed of remnants of the photoresist pattern 135 are located between the openings 140a as shown in FIG. 4B.

Figure 5A:
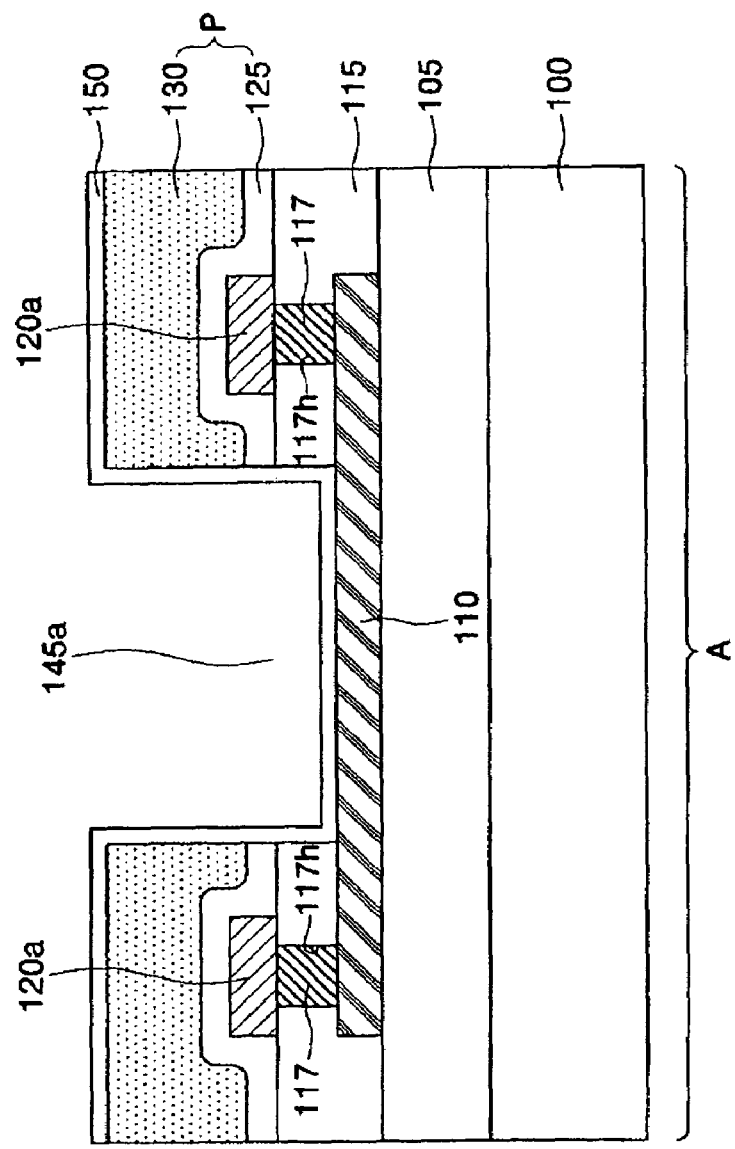
Figure 5B:
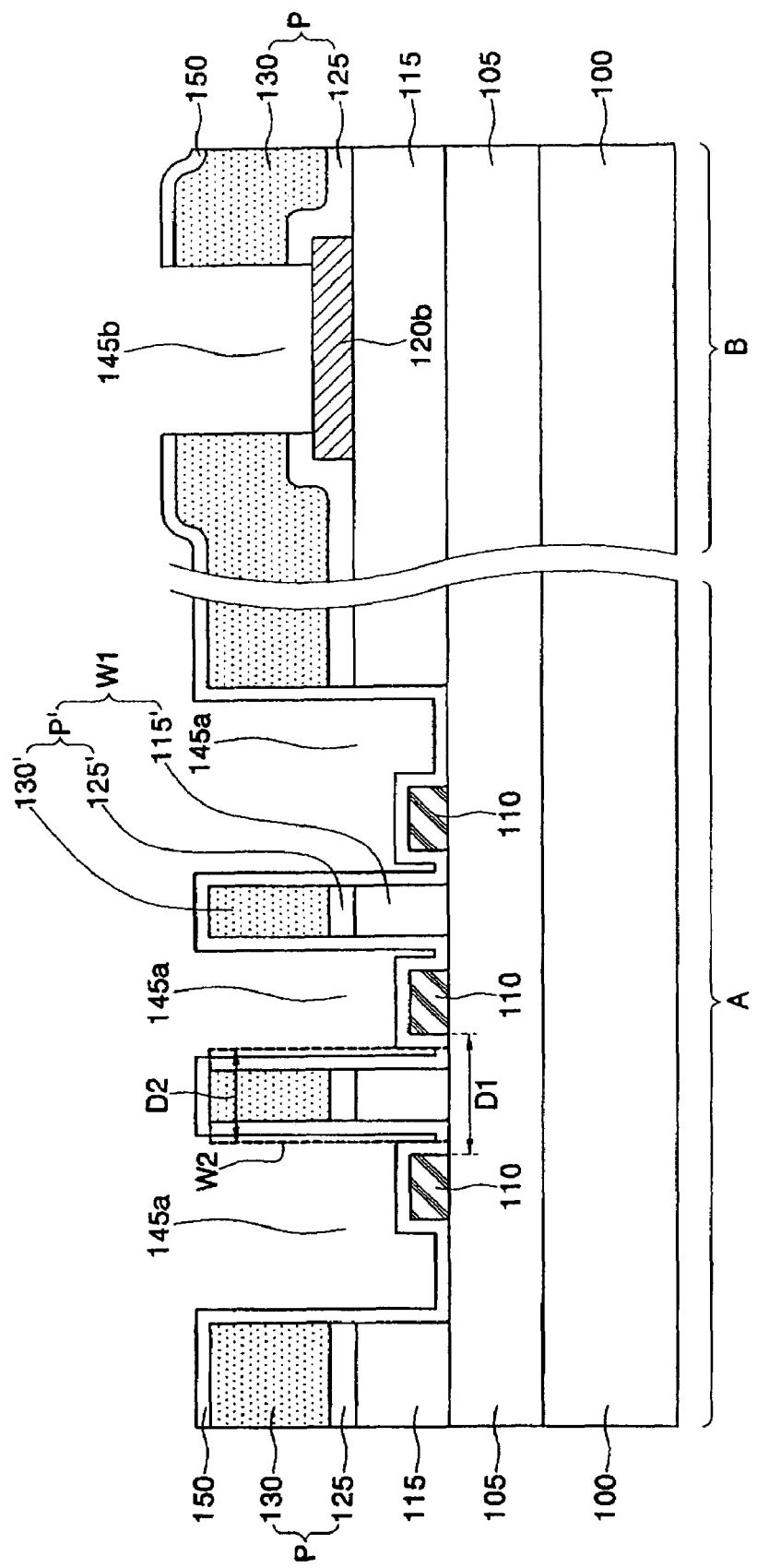

Referring to FIGS. 2, 5A, and 5B, fuse windows 145a that expose portions of a top surface and sidewall surfaces of the plurality of fuses 110, and fuse barrier patterns W1, W2 which are located between the each fuse are formed by sequentially etching the passivation layer P and the inter-metallic dielectric layer 115. A pad window 145b can be formed on the metal pad 120b contemporaneously with the fuse windows 145a and the fuse barrier patterns W1, W2. The fuse barrier patterns W1, W2 comprise, for example, an oxide layer including the patterned layers 115', 125' and a silicon nitride layer including patterned layer 130'. The width D2 of the fuse barrier pattern can be increased until it does not exceed the space D1 between the each fuse. As the result, fuse barrier patterns W1, W2 each of a maximum width D2 can be formed.

By forming the fuse barrier patterns W1, W2 between the fuses 110, the fuse barrier patterns W1, W2 operate to protect adjacent fuses 110 from exposure to damage that can otherwise occur when a selected fuse is blown by the laser beam. In other words, the fuse barrier pattern W1, W2 enables a safe and complete cut of a selected fuse, while mitigating or eliminating laser exposure to neighboring fuses. In addition, the profile of the fuse barrier pattern W1, W2 prevents any broken pieces of the blown fuse from migrating to thereby provide a path for shorting adjacent fuses; thus avoiding such shorting.

Thereafter, the photoresist pattern 135 is removed, and a capping layer 150 is formed on the plurality of fuses. The capping layer 150 can comprise, for example, a multi-layered structure comprising an inter-metallic dielectric layer and a passivation layer. The capping layer 150 can optionally comprise at least one material selected from a group consisting of a silicon oxide layer and silicon nitride layer. The capping layer 150 protects the plurality of fuses 110 exposed by the fuse window 145a from any contamination can otherwise occur by exposure to the external environment. Subsequently, the pad window 145b can be formed to exposed the underlying pad 120b by patterning the capping layer 150.

As disclosed above, the present invention confers several advantages. First, the fuse barrier pattern can protect non-selected fuses from damage that can otherwise occur due to inadvertent exposure by a laser beam when a neighboring selected fuse is cut by the laser beam. In this manner, the selected fuse can be cut by the laser beam completely and safely, without damaging neighboring fuses.

Second, the fuse barrier pattern can prevent broken pieces of the blown fuse from migrating to cause electrical shorting between the adjacent fuses.

Third, without the need for any additional processes, the fuse barrier pattern can be formed using a patterned mask at the time of opening the fuse window. As the result, the present invention can reduce the percentage of failing chips and reduce the unit cost of production.

While this invention has been particularly shown and described with reference to preferred embodiments thereof, it will be understood by those skilled in the art that various changes in form and detail may be made herein without departing from the spirit and scope of the invention as defined by the appended claims.

What is claimed is:

1. A method of fabricating a semiconductor device having a plurality of fuses, comprising:
   forming an inter-layer dielectric layer on a semiconductor substrate;
   forming a plurality of fuses on the inter-layer dielectric layer;
   forming an inter-metallic dielectric layer on the plurality of fuses and on the inter-layer dielectric layer;
   forming a passivation layer on the inter-metallic dielectric layer;
   forming fuse windows to expose portions of a top surface and sidewall of the plurality of fuses by etching the passivation layer and the inter-metallic dielectric layer; and
   forming a fuse barrier pattern between adjacent ones of the plurality of fuses, wherein the fuse barrier pattern and a sidewall of the fuse window have the same height.

2. A method of fabricating a semiconductor memory device as claimed in claim 1, wherein the fuse windows and the fuse barrier pattern are formed simultaneously.

3. A method of fabricating a semiconductor memory device as claimed in claim 1, wherein the fuse barrier pattern consists of a multi-layered structure of the same materials as those of the inter-metallic dielectric layer and the passivation layer.

4. A method of fabricating a semiconductor memory device as claimed in claim 1, further comprising:
   forming a photoresist pattern on the passivation layer before forming the fuse windows; and
   wherein the photoresist pattern is used as a mask when the inter-metallic dielectric layer and the passivation layer are etched.

5. A method of fabricating a semiconductor memory device as claimed in claim 1, further comprising:
   forming a pair of via holes at end regions of each of the plurality of fuses; and
   filling a conductive material in the via holes to connect the fuses with conductive lines formed on the inter-metallic dielectric layer.

6. A method of fabricating a semiconductor memory device as claimed in claim 1, further comprising forming a capping layer on the fuse barrier pattern and on the exposed portions of the plurality of fuses.

7. A method of fabricating a semiconductor memory device as claimed in claim 1, wherein the passivation layer comprises a silicon oxide layer and a silicon nitride layer.

8. A method of fabricating a semiconductor memory device as claimed in claim 1, wherein the inter-metallic dielectric layer comprises a silicon oxide layer.

9. A method of fabricating a semiconductor memory device as claimed in claim 6, wherein the capping layer is formed of a material selected from a group consisting of a silicon oxide layer and a silicon nitride layer.

10. A method of fabricating a semiconductor memory device as claimed in claim 6, wherein the capping layer is formed on the top surface and sidewall portions of the plurality of fuses.

11. A method of fabricating a semiconductor device having a plurality of fuses, comprising:

- providing a semiconductor substrate having a fuse region and a pad region;
- forming an inter-layer dielectric layer on the semiconductor substrate;
- forming a plurality of metallic fuses on the inter-layer dielectric layer in the fuse region;
- forming an inter-metallic dielectric layer on the plurality of fuses and on the inter-layer dielectric layer;
- forming a plurality of metal pads on the inter-metallic dielectric layer in the pad region;
- forming a passivation layer on the plurality of metal pads and on the inter-metallic dielectric layer;
- forming fuse windows to expose portions of a top surface and sidewall of the plurality of fuses by etching the passivation layer and inter-metallic dielectric layer;
- forming a fuse barrier pattern between adjacent ones of the plurality of fuses, wherein the fuse barrier pattern and a sidewall of the fuse window have the same height; and
- forming pad windows on the plurality of metal pads.

12. A method of fabricating a semiconductor memory device as claimed in claim 11, wherein the fuse windows, the fuse barrier pattern, and the pad windows are formed simultaneously by etching the passivation layer and the inter-metallic dielectric layer.

13. A method of fabricating a semiconductor memory device as claimed in claim 11, wherein the fuse barrier pattern consists of a multi-layered structure of the same material as those of the inter-metallic dielectric layer and the passivation layer.

14. A method of fabricating a semiconductor memory device as claimed in claim 11, further comprising:

- forming a photoresist pattern on the passivation layer before forming the fuse windows; and
- wherein the photoresist pattern is used as a mask when the inter-metallic dielectric layer and the passivation layer are etched.

15. A method of fabricating a semiconductor memory device as claimed in claim 11, further comprising:

- forming a pair of via holes at end regions of each of the plurality of fuses; and
- filling a conductive material in the via holes to connect the fuses with conductive lines formed on the inter-metallic dielectric layer.

16. A method of fabricating a semiconductor memory device as claimed in claim 11, further comprising forming a capping layer on the fuse barrier pattern and on the exposed portions of the plurality of fuses.

17. A method of fabricating a semiconductor memory device as claimed in claim 16, wherein the capping layer is formed of a material selected from a group consisting of a silicon oxide layer and a silicon nitride layer.

18. A method of fabricating a semiconductor memory device as claimed in claim 11, wherein the passivation layer comprises a silicon oxide layer and a silicon nitride layer.

19. A method of fabricating a semiconductor memory device as claimed in claim 11, wherein the inter-metallic dielectric layer comprises a silicon oxide layer.

* * * * *

UNITED STATES PATENT AND TRADEMARK OFFICE
CERTIFICATE OF CORRECTION

| | | |
|---|---|---|
| PATENT NO. | : 7,632,748 B2 | Page 1 of 1 |
| APPLICATION NO. | : 11/401435 | |
| DATED | : December 15, 2009 | |
| INVENTOR(S) | : Kim et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 654 days.

Signed and Sealed this

Second Day of November, 2010

David J. Kappos
*Director of the United States Patent and Trademark Office*